United States Patent [19]

Bistrian et al.

[11] Patent Number: 4,871,768

[45] Date of Patent: Oct. 3, 1989

[54] DIETARY SUPPLEMENT UTILIZING ω-3/MEDIUM CHAIN TRIGYLCERIDE MIXTURES

[75] Inventors: Bruce R. Bistrian, Ipswich; Vigen K. Babayan, Waban; George L. Blackburn, Jamaica; Edward A. Mascioli, Needham, all of Mass.

[73] Assignee: New England Deaconess Hospital Corporation, Boston, Mass.

[21] Appl. No.: 92,438

[22] Filed: Sep. 3, 1987

Related U.S. Application Data

[63] Continuation-in-part of Ser. No. 630,732, Jul. 12, 1984, Pat. No. 4,752,618.

[51] Int. Cl.$^4$ .......................................... A61K 31/225
[52] U.S. Cl. ................................ 514/547; 260/410.7; 260/410.8; 560/263
[58] Field of Search ..................... 514/547; 260/410.7, 260/410.8; 560/263

[56] References Cited

U.S. PATENT DOCUMENTS

| | | | |
|---|---|---|---|
| 3,232,941 | 2/1966 | Stein et al. | 260/410.7 |
| 3,268,340 | 8/1966 | Babayan et al. | |
| 3,494,944 | 2/1970 | Steden | 260/410.7 |
| 4,521,440 | 6/1985 | Lansbergen | 426/602 |
| 4,528,197 | 7/1985 | Blackburn | 514/552 |
| 4,607,052 | 8/1986 | Mendy et al. | 514/547 |
| 4,703,062 | 10/1987 | Blackburn et al. | 514/882 |

OTHER PUBLICATIONS

Osol et al–Dispensatory of the U.S.A. 25th edition (1955) pp. 346 & 347.

"Medium–Chain Triglycerides–Their Composition, Preparation, and Application", V. K. Babayan, Journal of the American Oil Chemists' Society, vol. 45, No. 1, pp. 23-25.

"Modification of Food to Control Fat Intake", Vigen K. Babayan, Journal of the American Oil Chemists' Society, vol. 51, No. 6, pp. 260-264 (1974).

"Medium Chain Length Fatty Acid Esters and Their Medical and Nutritional Applications", Vigen K. Babayan, Journal of the American Oil Chemists' Society, vol. 58, No. 1, pp. 49A-51 A (1981).

"Medium–Chain Triglycerides: an Update", Andre C. Bach, et al. Journal of Clinical Nutrition 36: Nov. 1982, pp. 950-962.

"Bailey's Industrial Oil and Fat Products", vol. 2, Fourth Edition, Robert R. Allen, et al., pp. 147-173.

Primary Examiner—Sam Rosen
Attorney, Agent, or Firm—Lahive & Cockfield

[57] ABSTRACT

A new dietary supplement has been developed which yields the benefits of both ω3 oils and medium chain triglycerides for lipid nutrition. A structured lipid containing ω3 fatty acids and medium chain fatty acids is also disclosed.

24 Claims, No Drawings

DIETARY SUPPLEMENT UTILIZING ω-3/MEDIUM CHAIN TRIGYLCERIDE MIXTURES cl REFERENCE RELATED APPLICATION

This application is a continuation-in-part of co-pending application Ser. No., 630,732, filed July 12, 1984, now U.S. Pat. No. 4,752,618.

BACKGROUND OF THE INVENTION

The field of lipid nutrition, including the public awareness of dietary modifications, has undergone a great number of changes in the last few years. Many people have replaced complex, saturated animal fats in their diets by polyunsaturated vegetable fats for health reasons, particularly in an attempt to control serum cholesterol levels. Most recently, fish oils have been suggested as a dietary supplement for cholesterol and triglyceride control and antithrombotic benefits. In addition, medium chain triglycerides ("MCT"), eight ($C_8$) and ten ($C_{10}$) carbon fatty acids bound to a glycerol backbone, have been used on an experimental basis, primarily in hospitals, as a nutrition source because of their rapid uptake and utilization by the body. Additional experimental work has been conducted with structured lipids, e.g., U.S. Pat. No. 4,528,197. However, none of these nutritional programs have been a panacea; there have been numerous problems with absorption of the fatty acids into the body and/or health problems in patients. These problems occur, in part, because of the type of fatty acid mixture chosen. Accordingly, there still remains a need for a better lipid nutrition supplement.

An understanding and/or modification of the lipids themselves and their delivery system is necessary for designing a better nutritional program. Lipids are primarily long chain polyunsaturated fatty acids which can be classified into three major groups: ω3, ω6 and ω9. The classes are based on the location of the double bond closest to the methyl end of the fatty acid; that is, if the closest double bond is between the third and fourth carbon atoms from the methyl group, the molecules are ω3 fatty acids while if the double bond is between the sixth and seventh carbon atoms, the molecules are classified as ω6 fatty acids. Man and other mammals can desaturate or elongate the fatty acid chains but cannot interconvert fatty acids from one family to another. Although most of the fatty acids consumed in normal nutrition have sixteen ($C_{16}$) or eighteen carbon ($C_{18}$) chains, the twenty or greater carbon fatty acids, whether ingested or made in the body, are the most important in terms of physiological functions. The ω9 fatty acids are primarily elongated to form the twenty carbon eicosatrienoic (C20:3ω9) while the most important twenty carbon ω6 fatty acid is arachidonic acid (C20:4ω6). The ω3 fatty acids are normally elongated and desaturated to form either the twenty carbon eicosapentaenoic (C20:5ω3) or the twenty-two carbon docosahexaenoic (C22:6ω3). The notation (C_:_ω_) indicates the number of carbon atoms in the chain, the number of double bonds, and the class of the fatty acid, respectively.

One of the reasons why the twenty carbon or greater fatty acids are important is their ability to act as substrates in the various prostanoid synthesis pathways, the chemical reactions which form prostaglandins from fatty acids. The first enzyme in this pathway is cyclo-oxygenase which has the ω6 fatty acid, arachidonic acid, as its primary substrate in mammals. In the platelets, the arachidonic acid is modified by the enzymes of the pathway to form thromboxane A2, a potent platelet aggregator and vasoconstrictor. In the endothelial cells, arachidonic acid is formed into prostacyclin I2, a vasodilator and platelet antiaggregator. In a number of tissues and organs, including the T-lymphocytes, arachidonic acid is formed into prostaglandin E2 which stimulates suppressor T cells and is immunosuppressive. Thromboxane A2, prostacyclin I2, and prostaglandin E2 are all classified as Type "2" prostaglandins.

The same enzyme, cyclo-oxygenase, can also use the ω3 fatty acids as substrates. In the platelets, eicosapentaenoic acid is formed into thromboxane $A_3$ while in the endothelial cells, it is converted into prostacyclin $I_3$. While prostacyclin $I_3$ has vasodilatory and platelet antiaggregating properties similar to prostacyclin I2, thromboxane A3 is only a weak vasoconstrictor and will not aggregate platelets. prostaglandin E3, formed in various tissues and organs including the T-lymphocytes, is not immunosuppressive. Thromboxane A3, prostacyclin $I_3$, and prostaglandin E3 are Type "3" prostaglandins.

Since both the ω3 and ω6 fatty acids can be used as substrates for the prostaglandin pathways, it may be possible to modify the prostaglandin mix in the body by modifying the dietary intake ratio of ω3 and ω6 fatty acids. While there have been some papers showing a change in the ratio of Type 2 to Type 3 by feeding a variety of ω3-rich fatty acid materials in place of ω6 rich foods, e.g., Sanders et al., *Clin. Sci.* 61:317–324 (1981), there is not a linear relationship. First, it appears that arachidonic acid is a preferred substrate for cyclo-oxygenase so the ω6 fatty acids in the diet are, therefore, used preferentially. Second, absorption of both ω3 and ω6 long chain fatty acids into the body is slow and may not be equal. Since there seems to be some correlation between an increase in the Type 3 prostaglandins and protection against blood clots and infection, optimal ways of increasing the Type 3/Type 2 prostaglandin ratio are important.

Lowering the ω6 fatty acid content and increasing the ω3 fatty acid content of the diets should not just improve response to infection, it may lead to an increase in platelet thromboxane $A_3$ levels. One theory of improving heart patient care is that the "stickiness" of the platelets is affected by the amount of thromboxane $A_2$, with a higher percentage of thromboxane A2 leading to "stickier" platelets. By providing more ω3 fatty acids to the clo-oxygenase-prostaglandin synthesis pathway, the thromboxane $A_3$ will be increased at the expense of thromboxane A2, leading to a lowering of "stickiness" of the platelets and a decrease in the probability of coronary thrombosis. Further, a decrease in thromboxane A2 levels has been found to lead to an increase in survival against the challenge of endotoxin. Cook, Wise and Halushka, *J. Clin. Invest.* 65:227 (1980).

The absorption of the long chain fatty acids into the body is relatively slow because they required initial hydrolysis and use the lymphatic system. In contrast, MCT's are rapidly absorbed by the body without initial intestinal hydrolysis and through the much faster portal system. It has been reported in "Medium Chain Triglycerides; an update", Bach and Babayan, *Am. J. of Cl. Nut.* 36:Nov. 1982, pp 951–962, that long chain fatty acids linked to the same glycerol backbone as MCT's will be absorbed faster than conventional triglycerides.

Because of faster absorption, MCT's are useful as a calorie source in the treatment of hospitalized patients. Some hospitalized patients, particularly critically ill patients, require total parenteral nutrition and have a high risk of infection. These patients often have difficulty in obtaining the proper amount of nutrients and energy from the diet; a diet which both minimizes the risk of infection and provides quick nutrition would be of vast benefit to these patients. These diets must provide the essential fatty acids, including a limited amount of specific ω6 fatty acids. Most currently available parenteral nutrition systems give much more of the essential fatty acids than is needed because they use soybean or safflower oil as the fatty acid source. These oils contain primarily polyunsaturated ω6 fatty acids but have little or no twenty carbon length ω3 fatty acid content. Since essential fatty acid nutrition requires that only 2 to 4% of the total calorie intake to be ω6 oils and most parenteral nutrition diets supply between 10 and 50% of the calorie intake as oils, there is a large excess of ω6 fatty acids being given on these diets.

While calories are important in the diet of a severely stressed patient, the form that calories are supplied in plays a significant role because carbohydrate energy sources, as opposed to fat sources, stimulate insulin release. Insulin release can be harmful in stress states because of problems with insulin resistance. Complications caused by excess carbohydrate content in the diet can include fatty liver, hyperglycemia, and respiratory failure due to excess carbon dioxide production. Usually 30 to 50% of the dietary calories should come from dietary fat to minimize these risks but if long chain fats, particularly having a chain length of sixteen carbons or greater, are used in this quantity, they are cleared very slowly from the circulation and can block the reticuloendothelial system. However, MCT's and structured lipids of MCT and LCT's provide additional fat calories and are rapidly cleared so there is no difficulty with the reticuloendothelial system. Further, and very importantly, the MCT's do not act as substrates for prostaglandin synthesis.

Accordingly, an object of the invention is to provide a method of minimizing the effects of infection and minimizing the effects of subsequent infection in at risk animals, particularly humans, by administering a diet which promotes resistance to infection as well as supplying a readily usable energy source.

Another object of the invention is to provide a dietary supplement which provides sufficient, highly usable nutrition to stressed patients while reducing the risks of infection.

A further object of the invention is to provide a method of treating patients having a high risk of infection with a dietary supplement that provides essential fatty acids while assisting in resistance to infection and heart problems.

A still further object of the invention is to provide a lipid source and a dietary supplement useful in treating stressed patients.

These and other objects and features of the invention will be apparent from the following description.

SUMMARY OF THE INVENTION

The present invention features a synthetic triglyceride (equivalent to structured lipid) which provides a high energy fat source and fatty acids which assist in fighting infection and atherosclerotic problems. The synthetic triglyceride has a glycerol backbone with three fatty acids linked thereto, with either one or two of said fatty acids being ω3 fatty acids and the remainder being fatty acids selected from a group consisting of caprylic acid ($C_8$), capric acid ($C_{10}$) and mixtures thereof. The preferred synthetic triglyceride has two caprylic or capric fatty acids and one long chain ω3 fatty acid. A most preferred synthetic triglyceride is a rearranged structured lipid which has the two caprylic or capric fatty acids on adjacent carbons of the glycerol backbone. Sources for the ω3 fatty acids are plant oils, marine plankton, fungal oils, and fish oils, preferably menhaden, salmon, anchovy or herring oils. The synthetic triglyceride can be replaced by a physical mixture of long chain ω3 fatty acids and MCT's with similar effects.

The invention also features a method of minimizing the effects of infection and minimizing the effects of subsequent infection in at risk patients by administering a diet containing 10 to 80% by weight of an oily fraction comprising glycerol, fatty acids, and combinations thereof, 50 to 90% of the fatty acids being caprylic acid, capric acid, or mixtures and 10 to 50% being ω3 fatty acids. The synthetic triglyceride may be a synthetic triglyceride as previously described or may constitute a physical mixture of MCT's and triglycerides rich in ω3 fatty acids. Oils which are concentrated to provide a high percentage of ω3 fatty acids per unit volume are a preferred ω3 fatty acid source.

The method of the invention is particularly useful for patients who are infected with wound infections, empyemas, bacteremias, abscesses, and septicemias. The method is also effective for patients who are suffering from surgical trauma, burns, malnutrition, starvation, aging, undergoing abdominal surgery, cancer, protein-malnourished patients, and those with secondary immunosuppression due to chemotherapy and diabetes mellitus. The synthetic triglyceride or the physical mix may be administered enterally or parenterally. A quantity of ω9 containing oils may also be present in the diet.

Another feature of the invention is a dietary supplement comprising 10 to 40% of an oily lipid fraction which has 50 to 90% by weight of medium chain fatty acids and 10 to 50% by weight of ω3 fatty acids. The supplement also may contain 1 to 2% by weight of an emulsifier, 1 to 3% of an osmolality modifier, and sterile water. The oily lipid fraction can be a physical mixture of the medium chain triglycerides and triglycerides rich in ω3 fatty acids or can be a rearranged structured lipid or synthetic triglyceride as previously described. The preferred emulsifiers are egg yolk phospholipids and soybean phospholipids while the preferred osmolality modifier is glycerol. The lipid fraction may also contain a fraction of ω9 fatty acids, particularly those oils rich in oleic acid, preferably high oleic safflower oil, high oleic sunflower oil, olive oil or canola oil.

The oils used to supply ω3 fatty acids should be rich in ω3 but should have a low concentration of vitamins A and D. If a non-concentrated oil is used, there should be no more than fifty international units (IU) of vitamin A per gram and no more than four IU of vitamin D per gram. If a concentrated oil is used, the oil could contain up to five hundred IU of vitamin A and forty IU of vitamin D per gram of oil.

Any diet within the scope of the invention would also include a small quantity of ω6 fatty acids to provide the essential fatty acids, particularly linoleic acid, needed for good nutrition. Other nutrients, including vitamins and minerals, may be included in the diet for complete nutrition.

DESCRIPTION

The present invention provides a family of lipids and lipid-based dietary supplements which provide a method of minimizing the risks and effects of infection in high risk patients as well as providing benefits to patients with heart problems. The mixtures of triglycerides rich in ω3 fatty acids and medium chain fatty acids described herein provide benefits in replacing the standard fatty acid composition of dietary supplements used in parenteral and enteral feedings. Survival to challenge with infection is also improved.

Conventional dietary supplements have primarily soybean or safflower oil as their lipid or fatty acid source. Soybean oil has approximately 53% ω6 fatty acids and only 8% ω3 fatty acids (as a linolemic acid only) while safflower oil has almost 78% ω6 fatty acids and substantially no ω3 fatty acids. In contrast, fish oils such as menhaden oil have 22% or more ω3 fatty acids and only 2 to 5% ω6 fatty acids. Replacing the predominantly ω6 fatty acids with predominantly ω3 fatty acids will promote prostaglandin Type 3 synthesis at the expense of prostaglandin Type 2 synthesis, yielding the intended physical benefits. The medium chain fatty acids do not function as precursors for prostaglandins of either type, leaving the ω3 fatty acids unopposed. Further, by using medium chain fatty acids in combination with ω3 fatty acids, a high calorie level and excellent absorption of fatty acids can be achieved without causing problems in the reticuloendothelial system. The more rapid uptake of lipid using an oil rich in ω3 fatty acids and MCT's should enhance membrane incorporation of the ω3 fats as well as limiting the impairment of the reticuloendothelial system possible with diets containing high levels of long chain fatty acids. Another benefit is that many infectious agents have endotoxins or elicit monokines, e.g., interleukin-1 and tumor necrosis factor, which increase the Type 2 prostaglandin level in the body. By giving a diet which promotes Type 3 prostaglandin synthesis at the expense to the Type 2 prostaglandins, survival from infection should be increased.

The following, non-limiting example will further show the efficacy of the present invention.

EXAMPLE 1.

This Example illustrates a diet based on a structured lipid of the present invention that can improve effectiveness against infection as compared with a conventional diet based on safflower oil. The structured lipid diet of the invention provides benefits in combating infection while providing excellent nutrition.

Table 1 lists the ingredients for a diet which is useful as a guinea pig demonstration diet. The oil fraction contained 145 grams of the MCT/menhaden ω3-structured lipid and 5 grams of safflower oil to prevent linoleic acid deficiency. This is a standard Reid-Briggs guinea pig diet except the oil content was raised so that the diet contains 15% by weight of lipid as opposed to the traditional 7.3%. Thirty-six percent of the dietary calories are lipid derived as compared with 15% in standard diets.

TABLE 1

| DIET COMPOSITION: MODIFIED REID-BRIGGS SEMI-PURIFIED GUINEA PIG DIET | |
|---|---|
| INGREDIENT | AMOUNT PER KILOGRAM (GRAMS) |
| Casein | 300 |
| Corn Starch | 200 |
| Sucrose | 89 |
| Glucose | 0 |
| Cellulose | 150 |
| Oil | 150 |
| Arginine | 3 |
| Salt Mix | 90 |
| Vitamin Mix | 10 |
| Choline Chloride | 4 |
| Ascorbic Acid | 4 |
| | 1,000 gr total |

The MCT/menhaden ω3-structured lipi can was made using standard procedures. The most common procedure uses sodium methylate as a catalyst for the interesterification reaction, forming the structured lipid. Because water "poisons" the sodium methylate catalyst, it is first necessary to dry the fats and/or oils used in the process. This is normally carried out by heating the fats to a temperature of 120–150° C. while under vacuum.

Once the fats are dry (having a water content of less than 0.001%), the fats are cooled to the reaction temperature of 60–80° C. Sodium methylate powder, approximately 0.2–0.4% by weight based on the fat content, is added to the dried fat and agitated for 30 to 60 minutes. A small amount of soda ash may be added at this time to neutralize free fatty acid. Once the reaction is completed, the catalyst is neutralized using $CO_2$ or phosphoric acid prior to water washing, refining and drying. Further details of this type of procedure can be found in a paper by Sreenivasan, J.A.O.C.S. 55:796–805 (1978).

Table 2 illustrates the specific fatty acid content of a standard safflower oil control diet and the MCT/menhaden oil ω3-structured lipid diet. The MCT diet contains more then 50% of its oil as C8–C10 fatty acids while the safflower oil control diet has none. Additionally, the safflower oil diet lacks the long chain polyunsaturated ω3 fatty acids, eicosapentaenoic and docosahexaenoic acids.

Diets of this type assist in infection protection and provide the other benefits of the invention. Although the exact ingredients and amounts would have to be modified for humans, this would lead one skilled in the art to the proper proportions for patients in need of lipid nutrition.

TABLE 2

| DIETARY OIL FATTY ACID COMPOSITION (IN PERCENT TOTAL FATTY ACIDS) | | | |
|---|---|---|---|
| FATTY ACID | | SAFFLOWER OIL | MCT/ MENHADEN OIL |
| C8:0 | Caprylic | 0 | 34.0 |
| C10:0 | Capric | 0 | 17.1 |
| C12:0 | Lauric | 0 | 0.2 |
| C14:0 | Myristic | .1 | 3.6 |
| C16:0 | Palmitic | 6.5 | 7.6 |
| C16:1ω7 | Palmitoleic | — | 5.0 |
| C18:0 | Stearic | 2.4 | 2.5 |
| C18:1ω9 | Oleic | 13.1 | 6.0 |
| C18:1ω7 | | — | 1.0 |
| C18:2ω6 | Linoleic | 77.7 | 1.2 |
| C20:4ω6 | Arachidonic | — | 0.5 |
| C20:4ω3 | | — | 1.5 |
| C20:5ω3 | Eicosapentaenoic | — | 14.5 |
| C22:5ω6 | | — | .4 |
| C22:5ω3 | | — | 1.0 |

TABLE 2-continued

DIETARY OIL FATTY ACID COMPOSITION
(IN PERCENT TOTAL FATTY ACIDS)

| FATTY ACID | | SAFFLOWER OIL | MCT/ MENHADEN OIL |
|---|---|---|---|
| C22:6ω3 | Docosahexaenoic | — | 3.6 |
| C24:1ω9 | | — | — |
| Other | | .2 | — |

EXAMPLE 2.

This Example illustrates one procedure for forming an oil emulsion which acts as a dietary supplement for patients which will enhance resistance to infection while providing good nutrition and an excellent energy source. patients who may benefit from such a supplement include those with secondary immunosuppression due to diabetes mellitus or chemotherapy, as well as those with other systemic stress. In these latter patients, the total polymorphonuclear leukocyte count is normally less than 1,000/mm$^3$. Another group of patients who could benefit are protein-malnourished patients. In these patients, the serum albumin level in plasma is normally less than 3.2 gm/dl or recent (within six months) weight loss of greater than 10% of original body weight has occurred.

The oil emulsion is made as follows. For each liter of emulsion, 100-300 gm of MCT/menhaden ω3-structured lipid is mixed with 11 gms of an emulsifier, e.g., egg yolk phospholipids USP, 22.5 gms of an osmolality modifier, e.g., glycerin USP, and sterile water USP to bring the volume to a liter. Specifically, the oil is added to a high shear mixer such as a Waring blender with steel blades operated at 1,600 RPM. The phospholipids are added slowly to the oil and mixed at high speed for six minutes. Sterile water is added to make a final volume of one liter in a steady stream to the phospholipid and oil mixture and emulsified for twenty minutes at 1,600 RPM. The attainment of the oil-in-water emulsion is confirmed by the "drop dispersion test". Emulsification is continued until the coarse oil emulsion disperses freely in water but not in oil.

The coarse emulsion is then passed through a high speed homogenizer five times until particle size is less than one micron. At that time, five more passes through the high speed homogenizer are performed and with each pass, glycerin is added to the emulsion. During the last five passes, additional water is added to make the final emulsion volume up to the one liter batch. Normally, all volumes are multiplied ten-fold and a ten liter batch is mixed at once.

Aliquots of the emulsion are set aside for measuring particle size which should be between 0.24 and 0.75 microns. The solutions are then passed through a five micron particle filter into sterile and pyrogen free evacuated containers. The emulsion is then sterilized at low temperature (105° C.) for twenty-five minutes. The solutions are cooled to room temperature and stored in the dark at 9° C. for one week. Prior to patient administration, the samples are retested for particle size and the presence of bacterial or endotoxin contamination. If the particle size is greater than one micron or the endotoxin concentration is greater than 1 ng, the batch of emulsion is discarded.

This dietary supplement can be used in patients who may be susceptible to a number of infectious agents. Examples of these infectious agents include *E. coli*, pseudomonas, or Klebsiella as gram negative bacteria; *Staphylococcus aureus* or albus as gram positive bacteria; *Herpes simplex* or *zoster* as viruses; and fungi such as Candida. Susceptibility to a variety of parasites can also be improved by this type of supplement.

While the method and dietary supplement disclosed herein will not necessarily prevent the onset of infection caused by these agents, it will promote survival of infected patients or animals. The use of a MCT/ω3-structured lipid incorporating ω3 fatty acids provides not only the ω3 benefits of promoting survival to infection but also the enhanced benefit of providing easily absorbed calories from the MCT's which do not promote insulin secretion as would a carbohydrate energy source. Further, the use of the MCT's together with the ω3 oils seem to promote the absorption and sparing of the ω3 oils.

The specific method and dietary supplement set forth herein are purely illustrative and those skilled in the art may determine other modifications and variations of these procedures. Such other modifications and variations are included within the scope of the following claims.

What is claimed is:

1. A synthetic triglyceride comprising a glycerol backbone having three fatty acids attached thereto, said fatty acids being selected from a first group consisting of ω3 fatty acids, and a second group consisting of caprylic acid, capric acid, and mixtures thereof;
   whereby at least one of said fatty acids is selected from said first group and at least one of said fatty acids is selected from said second group.

2. The synthetic triglyceride of claim 1 wherein two of said fatty acids are selected from said second group.

3. The synthetic triglyceride of claim 2 wherein said two fatty acids selected from said second group are bound to non-adjacent carbon atoms of said glycerol backbone.

4. The synthetic triglyceride of claim 3 comprising a rearranged structured lipid.

5. The synthetic triglyceride of claim 1 wherein said ω3 fatty acids are derived from plant oils, marine plankton oils, fungal oils, or fish oils.

6. The synthetic triglyceride of claim 5 wherein said fish oils are selected from a group consisting of menhaden oil, salmon oil, anchovy oil, herring oil, and mixtures thereof.

7. A method of minimizing the effects of infection and minimizing the effects of subsequent infection in at risk patients by administering a diet containing 10 to 80% by weight of an oily fraction, said oily fraction comprising a glycerol backbone having three fatty acids attached thereto, said fatty acids being selected from a first group consisting of ω3 fatty acids and from a second group consisting of caprylic acid, capric acid, and mixtures thereof, whereby at least one of said fatty acids is selected from said first group and at least one is selected from said second group.

8. The method of claim 7 wherein said synthetic triglyceride comprises two fatty acids selected from said second group and one fatty acid selected from said first group.

9. The method of claim 8 wherein said synthetic triglyceride has said ω3 fatty acid being in a central position on said glycerol backbone and comprises a rearranged structured lipid.

10. The method of claim 7 wherein said patients have wound infections, empyemas, bacteremias, abscesses, or septicemias.

11. The method of claim 7 wherein said patients are suffering from surgical trauma, burns, malnutrition, starvation, aging, cancer, or are protein-malnourished.

12. The method of claim 7 wherein said patients are undergoing abdominal surgery.

13. The method of claim 7 wherein said patients are suffering from secondary immunosuppression due to chemotherapy or diabetes mellitus.

14. The method of claim 7 wherein said diet is administered parenterally.

15. The method of claim 7 wherein said diet is administered enterally.

16. A dietary supplement comprising 10 to 40% by weight of an oily lipid fraction, said oily lipid fraction comprising 10 to 90% by weight of a synthetic triglyceride having a glycerol backbone and three fatty acids bound thereto, at least one of said fatty acids being said $\omega 3$ fatty acid and at least one of said fatty acids being selected from a group consisting of caprylic acid, capric acid, and mixtures thereof.

17. The dietary supplement of claim 16 further comprising 1-2% by weight of emulsifier selected from a group consisting of egg yolk phospholipids and soybean phospholipids.

18. The dietary supplement of claim 16 further comprising 1-3% by weight of an osmolality modifier.

19. The dietary supplement of claim 18 wherein said osmolality modifier comprises a glycerol.

20. The dietary supplement of claim 16 wherein said synthetic triglyceride further comprises $\omega 9$ fatty acids.

21. The dietary supplement of claim 20 wherein said $\omega 9$ fatty acids are selected from a group consisting of high oleic acid safflower oil, high oleic acid sunflower oil, olive oil, and canola oil.

22. The dietary supplement of claim 16 wherein said $\omega 3$ fatty acids are selected from a group of oils derived from fish oils, plant oils, fungal oils, marine plankton oils, and mixtures thereof.

23. The dietary supplement of claim 16 wherein said synthetic triglyceride has two fatty acids selected from the group consisting of caprylic acid, capric acid, and mixtures thereof and the third fatty acid being an $\omega 3$ fatty acid.

24. The dietary supplement of claim 23 wherein said synthetic triglycerides comprises a rearranged structured lipid.

* * * * *

UNITED STATES PATENT AND TRADEMARK OFFICE
CERTIFICATE OF CORRECTION

PATENT NO. : 4,871,768  Page 1 of 2
DATED : October 3, 1989
INVENTOR(S) : Bruce R. Bistrian, et al.

It is certified that error appears in the above-identified patent and that said Letters Patent is hereby corrected as shown below:

At Column 2, line 4 delete "A2" and insert --$A_2$--.

At Column 2, line 9 delete "E2" and insert --$E_2$--.

At Column 2, line 11 delete "A2" and insert --$A_2$--.

At Column 2, line 11 delete "I2" and insert --$I_2$--.

At Column 2, line 12 delete "E2" and insert --$E_2$--.

At Column 2, line 18 delete "I2" and insert --$I_2$--.

At Column 2, line 19 delete "A3" and insert --$A_3$--.

At Column 2, line 20 delete "E3" and insert --$E_3$--.

At Column 2, line 22 delete "A3" and insert --$A_3$--.

At Column 2, line 23 delete "E3" and insert --$E_3$--.

At Column 2, line 51 delete "clo-oxygenase" and insert --cyclo-oxygenase--.

At Column 2, line 56 delete "A2" and insert --$A_2$--.

At Column 5, line 19 delete "a linolemic acid" and insert --α-linolenic acid--.

UNITED STATES PATENT AND TRADEMARK OFFICE
CERTIFICATE OF CORRECTION

PATENT NO. : 4,871,768

DATED : October 3, 1989

INVENTOR(S) : Bruce R. Bistrian, et al.

It is certified that error appears in the above-identified patent and that said Letters Patent is hereby corrected as shown below:

At Column 6, line 17 delete "lipi" and insert --lipid--.

At Column 6, line 39 delete "C8-C10" and insert --$C_8$-$C_{10}$--.

At Column 6, lines 54-55 delete

"MCT MENHADEN" and insert --MCT/MENHADEN--.

At Column 7, line 17 delete "patients who" and insert --Patients who--.

Signed and Sealed this

Thirtieth Day of April, 1991

Attest:

HARRY F. MANBECK, JR.

Attesting Officer

Commissioner of Patents and Trademarks